(12) United States Patent
Humphreys et al.

(10) Patent No.: US 7,989,594 B2
(45) Date of Patent: Aug. 2, 2011

(54) MODIFIED ANTIBODY FAB FRAGMENTS

(75) Inventors: David Paul Humphreys, Maidenhead (GB); Sam Philip Heywood, High Wycombe (GB)

(73) Assignee: Celltech R & D Limited, Slough, Berkshire (GB)

( * ) Notice: Subject to any disclaimer, the term of this patent is extended or adjusted under 35 U.S.C. 154(b) by 1160 days.

(21) Appl. No.: 10/562,746

(22) PCT Filed: Jul. 1, 2004

(86) PCT No.: PCT/GB2004/002810
§ 371 (c)(1),
(2), (4) Date: Jun. 16, 2006

(87) PCT Pub. No.: WO2005/003169
PCT Pub. Date: Jan. 13, 2005

(65) Prior Publication Data
US 2006/0257394 A1 Nov. 16, 2006

(30) Foreign Application Priority Data

Jul. 1, 2003 (GB) .................................. 0315457.2
Aug. 20, 2003 (GB) .................................. 0319588.0

(51) Int. Cl.
*C07K 16/00* (2006.01)
*C12P 21/08* (2006.01)
*A61K 39/395* (2006.01)
*A61K 39/40* (2006.01)
*C12N 15/00* (2006.01)

(52) U.S. Cl. ............... 530/387.1; 530/387.3; 530/388.1; 530/391.1; 424/130.1; 424/133.1; 424/141.1; 424/178.1; 424/179.1

(58) Field of Classification Search .................. None
See application file for complete search history.

(56) References Cited

FOREIGN PATENT DOCUMENTS

| WO | WO89/01974 | 3/1989 |
|---|---|---|
| WO | WO93/06217 | 4/1993 |
| WO | 98/25971 A | 6/1998 |
| WO | WO 03/074679 | * 9/2003 |

OTHER PUBLICATIONS

Pritsch et al. J. Clin. Invest. 1996 98;10:2235-2243.*
Vitetta et al. Science 2006 313:308-309.*
Chapman et al. Nature Biotechnology, 1999 17:780-783.*
Singh, Rajeeva et al., "Labeling of Antibodies by in situ Modification of Thiol Groups Generated from Selenol-Catalyzed Reduction of Native Disulfide Bonds", Analytical Biochemistry, vol. 304, No. 2, May 15, 2002, pp. 147-156.
Leong, S. R. et al., "Adapting Pharmacokinetic Properties of a Humanized Anti-Interleukin-8 Antibody for Therapeutic Applications Using Site-Specific Pegylation", Cytokine, 2001, 16(3), 106-119.
Tout, N. L. et al., "Phage Display and Bacterial Expression of a Recombinant Fab Specific for Pseudomonas Aeruginosa Serotype O6 Lipopolysaccharide", Clinical and Diagnostic Laboratory Immunology, 1997, 4(2), 147-155.
Khawli, L. A. et al., "Stable, Genetically Engineered F(ab')2 Fragments of Chimeric TNT-3 Expressed in Mammalian Cells", Hybridoma and Hybridomics, 2002, 21(1), 11-18.
Alfthan, K. et al., "Efficient Secretion of Murine Fab Fragments by *Escherichia coli* is Determined by the First Constant Domain of the Heavy Chain", Gene., 1993, vol. 128, 203-209.
Wels, J. A. et al., Definition of Mouse gene IgG-3 heavy chain constant region, GenBank Acc. No. X00915, published Nov. 14, 2006 at http://www.ncbi.nlm.nih.gov/nuccore/51816, 3 sheets.
http://en.wikipedia.org/wiki/File :Engineered_monoclonal_antibodies. Svg, printed on Dec. 10, 2010, 1 sheet.
Chapman, "PEGylated antibodies and antibody fragments for improved therapy: a review", Advanced Drug Delivery Reviews, 54 (2002) 531-545.

* cited by examiner

*Primary Examiner* — Chun Dahle
(74) *Attorney, Agent, or Firm* — McDonnell Boehnen Hulbert & Berghoff LLP

(57) ABSTRACT

The present invention provides antibody Fab fragments in which the heavy chain constant region terminates at the interchain cysteine of $C_H1$. Also provided are antibody Fab fragments in which the heavy chain constant region terminates at the interchain cysteine of $C_H1$ to which one or more effector molecules are attached.

16 Claims, 5 Drawing Sheets

Figure 5

Figure 1:
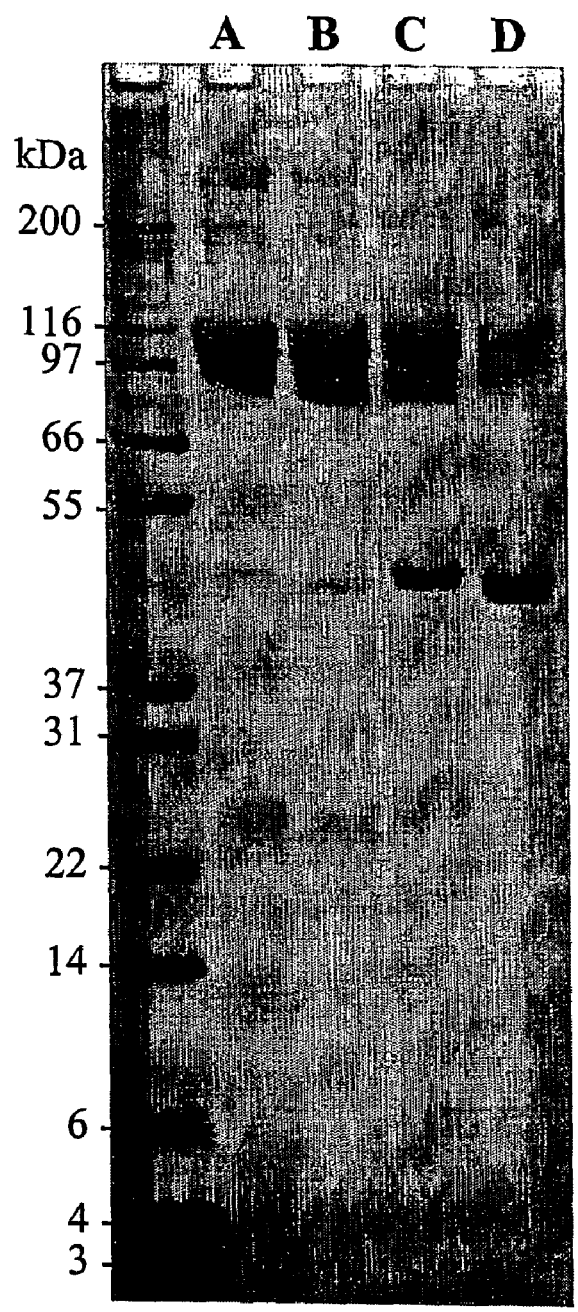

Seq ID No:1
ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSC

Seq ID No:2
KRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

Seq ID No: 3
KTTPPSVYPLAPGSAAQTNSMVTLGCLVKGYFPEPVTVTWNSGSLSSGVHTFPAVLQSDLYTLS
SSVTVPSSTWPSETVTCNVAHPASSTKVDKKIVPRDC

Seq ID No:4
DAAPTVSIFPPSSEQLTSGGASVVCFLNNFYPKDINVKWKIDGSERQNGVLNSWTDQDSKDSTY
SMSSTLTLTKDEYERHNSYTCEATHKTSTSPIVKSFNRGEC

Seq ID No:5
GCTTCTACAAAGGGCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGACGGTGTCGTGG
AACTCAGGCGCCCTGACCAGCGGCGTGCACACCTTCCCGGCTGTCCTACAGTCCTCAGGACT
CTACTCCCTCAGCAGCGTGGTGACCGTGCCCTCCAGCAGCTTGGGCACCCAGACCTACATCT
GCAACGTGAATCACAAGCCCAGCAACACCAAGGTCGACAAGAAAGTTGAGCCCAAATCTTG
TTAA

Seq ID No:6
AAACGTACGGTAGCGGCCCCATCTGTCTTCATCTTCCCGCCATCTGATGAGCAGTTGAAATC
TGGAACTGCCTCTGTTGTGTGCCTGCTGAATAACTTCTATCCCAGAGAGGCCAAAGTACAGT
GGAAGGTGGATAACGCCCTCCAATCGGGTAACTCCCAGGAGAGTGTCACAGAGCAGGACA
GCAAGGACAGCACCTACAGCCTCAGCAGCACCCTGACGCTGAGCAAAGCAGACTACGAGA
AACACAAAGTCTACGCCTGCGAAGTCACCCATCAGGGCCTGAGCTCACCAGTAACAAAAAG
TTTTAATAGAGGGGAGTGTTAA

Seq ID No.7
AAAAACGACACCCCCATCTGTCTATCCACTGGCCCCTGGATCTGCTGCCCAAACTAACTCCAT
GGTGACCCTGGGATGCCTGGTCAAGGGCTATTTCCCTGAGCCAGTGACAGTGACCTGGAAC
TCTGGATCCCTGTCCAGCGGTGTGCACACCTTCCCGGCTGTCCTGCAATCTGACCTCTACAC
TCTGAGCAGCTCAGTGACTGTCCCCTCCAGCACCTGGCCCAGCGAGACCGTCACCTGCAAC
GTTGCCCACCCGGCCAGCAGCACCAAGGTGGACAAGAAAATTGTGCCCAGGGATTGTTAA

Seq ID No:8
GATGCTGCACCAACTGTATCCATCTTCCCACCATCCAGTGAGCAGTTAACATCTGGAGGTGC
CTCAGTCGTGTGCTTCTTGAACAACTTCTACCCCAAAGACATCAATGTCAAGTGGAAGATTG
ATGGCAGTGAACGACAAAATGGCGTCCTGAACAGTTGGACTGATCAGGACAGCAAAGACA
GCACCTACAGCATGAGCAGCACCCTCACGTTGACCAAGGACGAGTATGAACGACATAACAG
CTATACCTGTGAGGCCACTCACAAGACATCAACTTCACCCATTGTCAAAAGCTTTAATAGAG
GGGAGTGTTAA

Seq ID NO:9
ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCAA

MODIFIED ANTIBODY FAB FRAGMENTS

The present invention relates to improved antibody fragments and more specifically provides improved antibody fragments to which one or more, preferably two or more, effector molecules are attached and methods for their production.

The high specificity and affinity of antibody variable regions make them ideal diagnostic and therapeutic agents, particularly for modulating protein:protein interactions. Antibody fragments are proving to be versatile therapeutic agents, as seen by the recent success of products such as ReoPro®. The targeting function encoded in Fv, Fab, Fab', F(ab)$_2$ and other antibody fragments can be used directly or can be conjugated to one or more effector molecules such as cytotoxic drugs, toxins or polymer molecules to increase efficacy. For example, since these fragments lack an Fc region they have a short circulating half-life in animals but this can be improved by conjugation to certain types of polymer such as polyethylene glycol (PEG). Increasing the size of the conjugated PEG has been shown to increase the circulating half-life from minutes to many hours and modification of a Fab' with PEG ranging from 5 kDa to 100 kDa has been demonstrated (Chapman et al., 1999, Nature Biotechnology, 17, 780-783; Leong et al., 2001, Cytokine, 16, 106-119; Chapman, 2002, Advanced Drug Delivery Reviews, 54, 531-545). PEGylated antibody fragments such as CDP870 are currently undergoing clinical trials where the effect of the conjugated PEG is to bring the circulating half-life to acceptable levels for therapy.

Effector molecules may be attached to antibody fragments by a number of different methods, including through aldehyde sugars or more commonly through any available amino acid side-chain or terminal amino acid functional group located in the antibody fragment, for example any free amino, imino, thiol, hydroxyl or carboxyl group. The site of attachment of effector molecules can be either random or site specific.

Random attachment is often achieved through amino acids such as lysine and this results in effector molecules being attached at a number of sites throughout the antibody fragment depending on the position of the lysines. While this has been successful in some cases the exact location and number of effector molecules attached cannot be controlled and this can lead to loss of activity for example if too few are attached and/or loss of affinity if for example they interfere with the binding site (Chapman 2002 Advanced Drug Delivery Reviews, 54, 531-545). As a result, controlled site specific attachment of effector molecules is usually the method of choice.

Site specific attachment of effector molecules is most commonly achieved by attachment to cysteine residues since such residues are relatively uncommon in antibody fragments. Antibody hinges are popular regions for site specific attachment since these contain cysteine residues and are remote from other regions of the antibody likely to be involved in antigen binding. Suitable hinges either occur naturally in the fragment or may be created using recombinant DNA techniques (See for example U.S. Pat. No. 5,677,425; WO98/25971; Leong et al., 2001 Cytokine, 16, 106-119; Chapman et al., 1999 Nature Biotechnology, 17, 780-783). Alternatively, or in addition, site specific cysteines may be engineered into the antibody fragment for example to create surface exposed cysteine(s) (U.S. Pat. No. 5,219,996).

Where effector molecules are to be site specifically attached via a cysteine, the target thiol in the antibody fragment is often capped by a small fermentation related peptide product such as glutathione or deliberately capped by a chemical additive used during antibody fragment extraction and purification such as 5,5'-dithiobis (2-nitrobenzoic acid) (DTNB). These capping agents need to be removed to activate the target (hinge or surface) thiol. Antibody fragments have a native interchain disulphide bond between the heavy and light chain constant regions ($C_H1$ and $C_L$) that has generally been regarded as critical in maintaining the stability and binding properties of the antibody. As a result the activation of the target hinge or surface thiol must be carried out with some care such that the inter $C_L$:$C_H1$ disulphide remains intact. Hence 'mild' reducing conditions are conventionally used to remove the thiol capping agent prior to reaction with the effector molecule. This is usually achieved by using thiol based reductants such as β-mercaptoethanol (β-ME), β-mercaptoethylamine (β-MA) and dithiothreitol (DTT). However, each of these reductants is known to be able to react with and stay attached to the cysteine which it is meant to reduce (Begg and Speicher, 1999 Journal of Biomolecular techniques, 10,17-20) thereby reducing the efficiency of effector molecule attachment. Hence, following reduction and reaction with effector molecules, a large proportion of the antibody fragments do not have any effector molecules attached and these have to be purified away from the antibody fragments that have the correct number of effector molecules attached. This poor efficiency of modification is clearly a disadvantage during the large-scale production of modified therapeutic antibody fragments where it is important that maximum production efficiency is achieved.

The present invention provides a new class of antibody Fab fragments to which effector molecules may be attached. A particular advantage of these fragments lies in the cysteine residues present in these fragments that may be used for site specific effector molecule attachment avoiding the need to engineer modified hinge regions and/or surface amino acid substitutions. When effector molecules are attached to the antibody Fab fragments of the present invention there are no inter-chain covalent linkages between the heavy and light chain. Despite the absence of any covalent linkage between the heavy and the light chain and the attachment of effector molecules, the fragments of the present invention perform comparably with wild type fragments in a number of in vitro and in vivo tests. Suprisingly these novel fragments have the same affinity for antigen and similar in vivo and in vitro stability as wild type fragments. A further advantage of these fragments lies in the ease of attachment of effector molecules to the fragments, and in particular, the efficiency of attachment. The fragments thus provide a low cost alternative to currently available fragments in which the native inter-chain covalent linkages are retained following effector molecule attachment.

Thus according to the present invention there is provided an antibody Fab fragment characterized in that the heavy chain constant region terminates at the interchain cysteine of $C_H1$.

The antibody Fab fragment of the present invention may be any heavy chain and light chain pair having a variable ($V_H$/$V_L$) and constant region ($C_H$/$C_L$). Preferably the heavy and light chain pair is $V_H$/$C_H1$ and $V_L$/$C_L$ covalently linked through interchain cysteines in the heavy and light chain constant regions. The term 'interchain cysteine' as used herein refers to a cysteine in the heavy or light chain constant region that would be disulphide linked to a cysteine in the corresponding heavy or light chain constant region encoded in a naturally occurring germline antibody gene. In particular the interchain cysteines of the present invention are a cysteine in the constant region of the light chain ($C_L$) and a cysteine in the first constant region of the heavy chain ($C_H1$) that are disulphide linked to each other in naturally occurring antibodies. Examples of such cysteines may typically be found at position 214 of the light chain and 233 of the heavy chain of human IgG1, 127 of the heavy chain of human IgM, IgE, IgG2, IgG3, IgG4 and 128 of the heavy chain of human IgD and IgA2B, as defined by Kabat et al., 1987, in Sequences of Proteins of Immunological Interest, US Department of Health and Human Services, NIH, USA. In murine IgG, interchain cysteines may be found at position 214 of the light chain and 235 of the heavy chain. It will be appreciated that the exact positions of these cysteines may vary from that of naturally occurring antibodies if any modifications, such as deletions, insertions and/or substitutions have been made to the antibody Fab fragment.

In the antibody Fab fragment of the present invention the heavy chain constant region terminates at the interchain cysteine of $C_H1$. Hence the last amino acid in the $C_H1$ domain of the antibody Fab fragment of the present invention is a cysteine. The antibody Fab fragment of the present invention in which the $C_H1$ domain is truncated may be prepared by any suitable method known in the art. For example, the antibody Fab fragment of the present invention may be obtained from any whole antibody, especially a whole monoclonal antibody, using any suitable enzymatic cleavage and/or digestion techniques, for example by treatment with pepsin or papain and c-terminal proteases. Preferably the antibody Fab fragment of the present invention is prepared by the use of recombinant DNA techniques involving the manipulation and re-expression of DNA encoding antibody variable and constant regions. Standard molecular biology techniques may be used to modify, add or delete further amino acids or domains as desired. Any alterations to the variable or constant regions are still encompassed by the terms 'variable' and 'constant' regions as used herein. Preferably PCR is used to introduce a stop codon immediately following the codon encoding the interchain cysteine of $C_H1$, such that translation of the $C_H1$ domain stops at the interchain cysteine. Methods for designing suitable PCR primers are well known in the art and the sequences of antibody $C_H1$ domains are readily available (Kabat et al., supra). Alternatively stop codons may be introduced using site-directed mutagenesis techniques such as those described in White (Ed.), PCR Protocols: Current Methods and Applications (1993). The antibody fragment starting material of the present invention may be derived from any antibody isotype including for example IgG, IgM, IgA, IgD and IgE and subclasses thereof including for example IgG1, IgG2, IgG3 and IgG4. Preferably the antibody Fab fragment of the present invention is derived from IgG1. The antibody fragment starting material may be obtained from any species including for example mouse, rat, rabbit, pig, hamster, camel, llama, goat or human. Parts of the antibody fragment may be obtained from more than one species for example the antibody fragments may be chimeric. In one example the constant regions are from one species and the variable regions from another. The antibody fragment starting material may also be modified. In one example the variable region of the antibody fragment has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and optionally one or more framework amino acids from one antibody and the remainder of the variable region domain from a second antibody. The methods for creating and manufacturing these antibody fragments are well known in the art (see for example, Boss et al., U.S. Pat. No. 4,816,397; Cabilly et al., U.S. Pat. No. 6,331,415; Shrader et al., WO 92/02551; Orlandi et al., 1989, Proc.Natl.Acad.Sci. USA, 86, 3833; Riechmann et al., 1988, Nature, 322, 323; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

The antibody fragment of the present invention will in general be capable of selectively binding to an antigen. The antigen may be any cell-associated antigen, for example a cell surface antigen on cells such as bacterial cells, yeast cells, T-cells, endothelial cells or tumour cells, or it may be a soluble antigen. Antigens may also be any medically relevant antigen such as those antigens upregulated during disease or infection, for example receptors and/or their corresponding ligands. Particular examples of cell surface antigens include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), MHC Class I and MHC Class II antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof.

The present invention provides an antibody Fab fragment characterized in that the heavy chain constant region terminates at the interchain cysteine of $C_H1$. In one embodiment the heavy chain and light chain constant regions are derived from human IgG1. In one embodiment the present invention provides an antibody Fab fragment in which the heavy chain constant region comprises or consists of the amino acid sequence provided in SEQ ID NO: 1. The present invention also provides an antibody Fab fragment in which the heavy chain constant region comprises or consists of the amino acid sequence provided in SEQ ID NO:1 and the light chain constant region comprises or consists of the amino acid sequence provided in SEQ ID NO:2. All sequences and their SEQ ID numbers are provided in FIG. 5.

In another embodiment the heavy and light chain constant regions are derived from murine IgG1. In this aspect the present invention provides an antibody Fab fragment in which the heavy chain constant region comprises or consists of the amino acid sequence provided in SEQ ID NO: 3. The present invention also provides an antibody Fab fragment in which the heavy chain constant region comprises or consists of the amino acid sequence provided in SEQ ID NO:3 and the light chain constant region comprises or consists of the amino acid sequence provided in SEQ ID NO:4.

The present invention also provides an antibody Fab fragment wherein the constant region of the heavy chain comprises or consists of a sequence having at least 90% identity or similarity to the sequence given in SEQ ID NO:1.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Preferably, the antibody Fab fragment of this aspect of the present invention comprises a heavy chain, wherein the constant region of the heavy chain comprises a sequence having at least 90%, 95% or 98% identity or similarity to the sequence given in SEQ ID NO:1.

The present invention also provides an antibody Fab fragment wherein the constant region of the heavy chain comprises or consists of a sequence having at least 90% identity or similarity to the sequence given in SEQ ID NO:1 and the constant region of the light chain comprises or consists of a sequence having at least 90% identity or similarity to the sequence given in SEQ ID NO:2. Preferably, the antibody Fab fragment of this aspect of the present invention comprises a heavy chain, wherein the constant region of the heavy chain comprises a sequence having at least 90%, 95% or 98% identity or similarity to the sequence given in SEQ ID NO:1 and a light chain wherein the constant region of the light chain comprises a sequence having at least 90%, 95% or 98% identity or similarity to the sequence given in SEQ ID NO:2.

The present invention also provides an antibody Fab fragment wherein the constant region of the heavy chain comprises or consists of a sequence having at least 90% identity or similarity to the sequence given in SEQ ID NO:3. In one embodiment, the present invention provides an antibody Fab fragment wherein the constant region of the heavy chain comprises or consists of a sequence having at least 90% identity or similarity to the sequence given in SEQ ID NO:3 and the constant region of the light chain comprises or consists of a sequence having at least 90% identity or similarity to the sequence given in SEQ ID NO:4. Preferably, the antibody Fab fragment of this aspect of the present invention comprises a heavy chain, wherein the constant region of the heavy chain comprises a sequence having at least 90%, 95% or 98% identity or similarity to the sequence given in SEQ ID NO:3 and a light chain wherein the constant region of the light chain comprises a sequence having at least 90%, 95% or 98% identity or similarity to the sequence given in SEQ ID NO:4.

Nucleic acid sequences which encode the the amino acid sequences provided in SEQ ID NOs 1-4 can be designed using known methods in the art. In one embodiment the invention provides isolated DNA sequences encoding the heavy and/or light chain constant regions provided in SEQ ID NOs 1-4. In one embodiment the nucleic acid sequences encoding the amino acid sequences provided in SEQ ID NOs 1, 2, 3 and 4 are those given in SEQ ID NOs 5, 6, 7 and 8 respectively.

The present invention also relates to a cloning or expression vector comprising one or more DNA sequences of the present invention. Accordingly, provided is a cloning or expression vector comprising one or more DNA sequences encoding an antibody Fab fragment of the present invention. In particular cloning or expression vectors of the present invention comprise one or more DNA sequences encoding the antibody constant regions of the present invention, as provided in SEQ ID NOs 5-8. In one embodiment the vector comprises the sequence given in SEQ ID NO:5 and SEQ ID NO:6. In another embodiment the vector comprises the sequence given in SEQ ID NO:7 and SEQ ID NO:8.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing Also provided by the present invention is a host cell expressing an antibody Fab fragment in which the $C_H1$ domain terminates at the interchain cysteine. Any suitable host cell/vector system may be used for the expression of the DNA sequences encoding the antibody Fab of the present invention. Also provided therefore is a host cell comprising one or more cloning or expression vectors comprising one or more DNA sequences encoding an antibody fragment of the present invention. In particular host cells comprising cloning or expression vectors of the present invention comprising one or more DNA sequences encoding the antibody constant regions of the present invention, as provided in SEQ ID NOs 5-8. Bacterial, for example E.coli, and other microbial systems may be used or eukaryotic, for example mammalian host cell expression systems may also be used. Suitable E.coli strains for use in the present invention may be naturally occurring strains or mutated strains capable of producing recombinant proteins. Examples of specific host E.coli strains include MC4100, TG1, TG2, DHB4, DH5α, DH1, BL21, XL1Blue and W3110 (ATCC 27,325). Suitable mammalian host cells include CHO, myeloma or hybridoma cells. Also provided is a method of producing the antibody Fab fragment of the present invention comprising culturing the host cell expressing the antibody Fab fragment of the present invention and isolating said fragment. Once produced in the host cell the antibody Fab fragment may be extracted and purified using any suitable method known in the art. Heat extraction may be used as described in U.S. Pat. No. 5,665,866 due to the presence of the interchain disulphide bond. Suitable purification methods include but are not limited to size exclusion, hydrophobic interaction chromatography, protein A, G or L affinity chromatography and ion exchange.

If desired, the antibody Fab fragment of the present invention may have one or more effector molecules attached to it. The term effector molecule as used herein includes, for example, antineoplastic agents, drugs, toxins (such as enzymatically active toxins of bacterial or plant origin and fragments thereof e.g. ricin and fragments thereof) biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Particular antineoplastic agents include cytotoxic and cytostatic agents for example alkylating agents, such as nitrogen mustards (e.g. chlorambucil, melphalan, mechlorethamine, cyclophosphamide, or uracil mustard) and derivatives thereof, triethylenephosphoramide, triethylenethiophosphor-amide, busulphan, or cisplatin; antimetabolites, such as methotrexate, fluorouracil, floxuridine, cytarabine, mercaptopurine, thioguanine, fluoroacetic acid, or fluorocitric acid, antibiotics, such as bleomycins (e.g. bleomycin sulphate), doxorubicin, daunorubicin, mitomycins (e.g. mitomycin C), actionmycins (e.g. dactinomycin) plicamyin, calichaemicin and derivatives thereof, or esperamicin and derivatives thereof; mitotic inhibitors, such as etoposide, vincristine or vinblastine and derivatives thereof; alkaloids such as ellipticine; polyols such as taxicin-I or taxicin-II; hormones, such as androgens (e.g. dromostanolone or testolactone), progestins (e.g. megestrol acetate or medroxyprogesterone acetate), estrogens (e.g. dimethylstilbestrol diphosphate, polyestradiol phosphate or estramustine phosphate) or antiestrogens (e.g. tamoxifen); anthraquinones, such as mitoxantrone, ureas, such as hydroxyurea; hydrazines, such as procarbazine; or imidazoles, such as dacarbazine.

Chelated metals include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd and $^{47}$Sc.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in International Patent Specification No. WO 92/22583); and polyamides, especially desferriox-amine and derivatives thereof.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerytbrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Synthetic or naturally occurring polymers for use as effector molecules include, for example optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol) such as methoxypoly(ethyleneglycol) or derivatives thereof.

"Derivatives" as used herein is intended to include reactive derivatives, for example thiol-selective reactive groups such as an α-halocaraboxylic acid or ester, e.g. iodoacetamide, an imide, e.g. maleimide, a vinyl sulphone or disulphide maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50,000 Da, preferably from 5,000 to 40,000 Da and more preferably from 10,000 to 40,000 Da and 20,000 to 40,000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5,000 Da. For applications where the product remains in the circulation, it may be advantageous to use a higher molecular weight polymer, for example having a molecular weight in the range from 20,000 Da to 40,000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 10,000 Da to about 40,000 Da.

The polymers of the present invention may be obtained commercially (for example from Nippon Oil and Fats; Nektar Therapeutics) or may be prepared from commercially available starting materials using conventional chemical procedures.

Effector molecules may be attached using standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include for example those described in International Patent Specification numbers WO 93/06231, WO92/22583, WO90/09195, WO89/01476, WO9915549 and WO03031581. Alternatively, where the effector molecule is a protein or polypeptide the linkage may be achieved using recombinant DNA procedures, for example as described in European Patent Specification No. 392745.

The effector molecules may be attached to the antibody fragment of the present invention through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods. See for example U.S. Pat. No. 5,219,996. Preferably effector molecules are covalently linked through a thiol group of a cysteine residue located in the antibody fragment, either naturally or engineered. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used.

It will be appreciated that where there are two or more effector molecules attached to the antibody fragment these may be identical or different and may be attached to the antibody fragment at different sites. It will also be appreciated that two or more effector molecules may be attached to the antibody fragment at a single site by the use for example of a branched connecting structure to link two or more effector molecules and provide a single site of attachment.

In a preferred aspect of the present invention at least one of the effector molecules attached to the antibody fragment is a polymer molecule, preferably PEG or a derivative thereof. As regards attaching poly(ethyleneglycol) (LEG) moieties in general, reference is made to "Poly(ethyleneglycol) Chemistry, Biotechnical and Biomedical Applications", 1992, J. Milton Harris (ed), Plenum Press, New York; "Poly(ethyleneglycol) Chemistry and Biological Applications", 1997, J. Milton Harris and S. Zalipsky (eds), American Chemical Society, Washington DC and "Bioconjugation Protein Coupling Techniques for the Biomedical Sciences", 1998, M. Aslam and A. Dent, Grove Publishers, New York.

Preferably all the effector molecules attached to the Fab fragment of the present invention are PEG and each molecule is covalently linked via a maleimide group to one or more thiol groups in the antibody fragment. The PEG may be any straight or branched molecule in an average molecular weight range from 500 Da to 50,000 Da, preferably from 5,000 to 40,000 Da and more preferably from 10,000 to 40,000 Da and 20,000 to 40,000 Da. To attach branched PEG molecules, a lysine residue is preferably covalently linked to the maleimide group. To each of the amine groups on the lysine residue is preferably attached a methoxypoly(ethyleneglycol) polymer. In one example the molecular weight of each polymer attached to the lysine is approximately 20,000 Da and the total molecular weight of the entire polymer molecule is therefore approximately 40,000 Da. Preferably the PEG molecules attached to the Fab fragment of the present invention are linear.

One or more effector molecules may be attached to the antibody Fab fragment of the present invention. In a preferred aspect at least two effector molecules are attached to the Fab fragment, one to a cysteine in the light chain constant region and one to a cysteine in the heavy chain constant region. Preferably the cysteine residues to which the effector molecules are attached would otherwise be linked to each other by a disulphide bond if the effector molecules were not attached. Suitable cysteines for attachment include naturally occurring cysteines present in the light and/or heavy chain constant region such as the interchain cysteines. In a preferred aspect of the invention an effector molecule is attached to the interchain cysteine of $C_L$ and the interchain cysteine of $C_H1$ in the antibody Fab fragment. In one embodiment the interchain cysteine of $C_L$ to which an effector molecule is attached is at position 214 of the light chain and the interchain cysteine of $C_H1$ to which an effector molecule is attached is at position 233 of the heavy chain. In another embodiment where the constant regions are derived from murine IgG1, the interchain cysteine of $C_L$ to which an effector molecule is attached is at position 214 of the light chain and the interchain cysteine of $C_H1$ to which an effector molecule is attached is at position 235 of the heavy chain. Other suitable cysteines include those that have been engineered into the constant regions using recombinant DNA techniques. For example two cysteines may be engineered into the antibody fragment, one in each of the heavy and light chain constant regions, preferably at positions whereby they can form a disulphide linkage with each other.

Particular fragments according to this aspect of the invention include those where:
(i) the cysteine residues in the heavy and light chain constant regions which are attached to effector molecules would otherwise be linked to each other via a disulphide bond if the effector molecules were not attached or
(ii) the light chain cysteine to which an effector molecule is attached is the interchain cysteine of $C_L$ and the heavy chain cysteine to which an effector molecule is attached is the interchain cysteine of $C_H1$ During attachment of effector molecules to cysteines in the antibody Fab fragment of the present invention any covalent linkages between the cysteines are removed, as described herein, using a reducing agent. In such fragments the heavy chain is no longer covalently bonded to the light chain and the disulphide linkage found in naturally occurring antibodies between the interchain cysteine of $C_L$ and the interchain cysteine of $C_H1$ is absent.

Also provided by the present invention therefore is a method for attaching effector molecules to the antibody Fab fragments of the present invention, said method comprising:
a) Treating an antibody Fab fragment of the present invention with a reducing agent capable of generating a free thiol group in a cysteine of the heavy and light chain constant region
b) Reacting the treated fragment with an effector molecule
In a preferred aspect the method comprises:
a) Reducing the interchain disulphide bond between the interchain cysteine of $C_H1$ and the interchain cysteine of $C_L$ in the antibody Fab fragment of the present invention
b) Reacting the treated fragment with an effector molecule
The methods provided by the present invention enable one or more effector molecule(s) to be attached to cysteines in the antibody fragment, in particular to cysteines in the constant region. Two or more effector molecules can be attached to the antibody fragment using the methods described herein either simultaneously or sequentially by repeating the method.

Additional effector molecules may be attached elsewhere in the antibody fragment, in particular the constant regions. The methods of the present invention therefore also extend to one or more steps before and/or after the reduction methods described above in which further effector molecules are attached to the antibody fragment using any suitable method as described previously, for example via other available amino acids side chains such as amino and imino groups.

The reducing agent for use in the methods of the present invention is any reducing agent capable of reducing cysteines in the antibody Fab fragment of the present invention to produce free thiols. Preferably the reducing agent reduces the interchain disulphide bond between cysteines of the heavy and light chain constant regions, for example, between the interchain cysteine of $C_L$ and the interchain cysteine of $C_H1$, in order to allow attachment of effector molecules to said cysteines. As the antibody Fab fragments of the present invention surprisingly have no requirement for the interchain disulphide bond stronger reducing agents can be used than are conventionally used with wild type antibody fragments which retain the interchain disulphide bond. As a result a higher number of Fab molecules with free thiols are produced and a higher proportion of the antibody fragments are correctly modified i.e. the correct number of effector molecules are attached. In addition, the terminal interchain cysteine of $C_H1$ in the antibody Fab fragments of the present invention is more highly accessible for effector molecule attachment and reduction than in conventional Fab fragments where there may be steric or local electrostatic effects due to the presence of the upper hinge or other amino acids C-terminal to the $C_H1$ interchain cysteine. The antibody fragments of the present invention can therefore be modified more efficiently and cost effectively than conventional antibody fragments. It will be clear to a person skilled in the art that suitable reducing agents may be identified by determining the number of free thiols produced after the antibody fragment is treated with the reducing agent. Methods for determining the number of free thiols are well known in the art, see for example Lyons et al., 1990, Protein Engineering, 3, 703. Reducing agents for use in the present invention are widely known in the art for example those described in Singh et al., 1995, Methods in Enzymology, 251, 167-73. Particular examples include thiol based reducing agents such as reduced glutathione (GSH), β-mercaptoethanol (β-ME), β-mercaptoethylamine (β-MA) and dithiothreitol (DTT). Other methods for reducing the antibody fragments of the present invention include using electrolytic methods, such as the method described in Leach et al., 1965, Div. Protein. Chem, 4, 23-27 and using photoreduction methods, such as the method described in Ellison et al., 2000, Biotechniques, 28 (2), 324-326. Preferably however, the reducing agent for use in the present invention is a non-thiol based reducing agent capable of liberating one or more thiols in an antibody fragment. Preferably the non-thiol based reducing agent is capable of liberating the interchain thiols in an antibody fragment. Preferred reducing agents for use in the present invention are trialkylphosphine reducing agents (Ruegg U T and Rudinger, J., 1977, Methods in Enzymology, 47, 111-126; Burns J et al., 1991, J. Org. Chem, 56, 2648-2650; Getz et al., 1999, Analytical Biochemistry, 273, 73-80; Han and Han, 1994, Analytical Biochemistry, 220, 5-10; Seitz et al., 1999, Euro. J. Nuclear Medicine, 26, 1265-1273), particular examples of which include tris(2-carboxyethyl) phosphine (TCEP), tris butyl phosphine (TBP), tris-(2-cyanoethyl) phosphine, tris-(3-hydroxypropyl) phosphine (THP) and tris-(2-hydroxyethyl) phosphine. Most preferably the reducing agent for use in the present invention is either TCEP or THP. It will be clear to a person skilled in the art that the concentration of reducing agent for use in the present invention can be determined empirically, for example, by varying the concentration of reducing agent and measuring the number of free thiols produced. Typically the reducing agent for use in the present invention is used in excess over the antibody fragment for example between 2 and 1000 fold molar excess. Preferably the reducing agent is in 2, 3, 4, 5, 10, 100 or 1000 fold excess. In one embodiment the reductant is used at between 2 and 5 mM.

The modified antibody Fab fragments according to the invention may be prepared by reacting an antibody Fab fragment as described herein containing at least one reactive cysteine residue with an effector molecule, preferably a thiol-selective activated effector molecule. The reactions in steps (a) and (b) of the method described above may generally be performed in a solvent, for example an aqueous buffer solution such as acetate or phosphate, at around neutral pH, for example around pH 4.5 to around pH 8.5, typically pH 4.5 to 8, suitably pH6 to 7. The reaction may generally be performed at any suitable temperature, for example between about 5° C. and about 70° C., for example at room temperature. The solvent may optionally contain a chelating agent such as EDTA, EGTA, CDTA or DTPA. Preferably the solvent contains EDTA at between 1 and 5 mM, preferably 2 mM. Alternatively or in addition the solvent may be a chelating buffer such as citric acid, oxalic acid, folic acid, bicine, tricine, tris or ADA. The effector molecule will generally be employed in excess concentration relative to the concentration of the antibody fragment. Typically the effector molecule is in between 2 and 100 fold molar excess, preferably 5, 10 or 50 fold excess.

Where necessary, the desired product containing the desired number of effector molecules may be separated from any starting materials or other product generated during the production process by conventional means, for example by chromatography techniques such as ion exchange, size exclusion, protein A, G or L affinity chromatography or hydrophobic interaction chromatography.

Also provided by the present invention is a mixture containing two or more antibody Fab fragments, characterized in that the mixture is enriched for Fab fragments in which the heavy chain constant domain terminates at the interchain cysteine of $C_H1$, the heavy chains in the fragments are not covalently bonded to the light chains and the fragments have an effector molecule attached to a cysteine in the light chain and the heavy chain constant region. Said mixture may be produced using the methods provided by the present invention. By 'enriched' we mean that the antibody Fab fragment with the desired number of effector molecules attached accounts for 50% or greater of the mixture. Preferably the antibody Fab fragment with the desired number of effector molecules attached accounts for between 50 and 99% of the mixture. Preferably the mixtures are enriched by greater than 50%, preferably greater than 60%, more preferably greater than 70%. The proportion of such mixtures containing the antibody Fab fragment with the desired number of effector molecules may be determined by using the size exclusion HPLC methods described herein.

The antibody fragments according to the invention may be useful in the detection or treatment of a number of diseases or disorders. Such diseases or disorders may include those described under the general heading of infectious disease, e.g. bacterial infection; fungal infection; inflammatory disease/autoimmunity e.g. rheumatoid arthritis, osteoarthritis, inflammatory bowel disease; cancer; allergic/atopic disease e.g. asthma, eczema; congenital disease, e.g. cystic fibrosis, sickle cell anemia; dermatologic disease e.g. psoriasis; neurologic disease, e.g. multiple sclerosis; transplants e.g. organ transplant rejection, graft-versus-host disease; and metabolic/idiopathic disease e.g. diabetes.

The antibody fragments according to the invention may be formulated for use in therapy and/or diagnosis and according to a further aspect of the invention we provide a pharmaceutical composition comprising an antibody Fab fragment in which the heavy chain constant region terminates at the interchain cysteine of $C_H1$ together with one or more pharmaceutically acceptable excipients, diluents or carriers. Also provided is a pharmaceutical composition comprising an antibody Fab fragment in which the heavy chain constant region terminates at the interchain cysteine of $C_H1$, the heavy chain is not covalently bonded to the light chain and the fragment has an effector molecule attached to a cysteine in the light chain and the heavy chain constant region, together with one or more pharmaceutically acceptable excipients, diluents or carriers.

The present invention will now be described by way of example only, in which reference is made to:

FIG. 1: Non-reducing SDS-PAGE of PEGylated g163 Fab in which the heavy chain constant region terminates at the interchain cysteine of $C_H1$. Lane B shows g163 Fab with PEG attached following reduction with TCEP. Lane D shows g163 Fab with PEG attached following reduction with THP.

Figure 2:
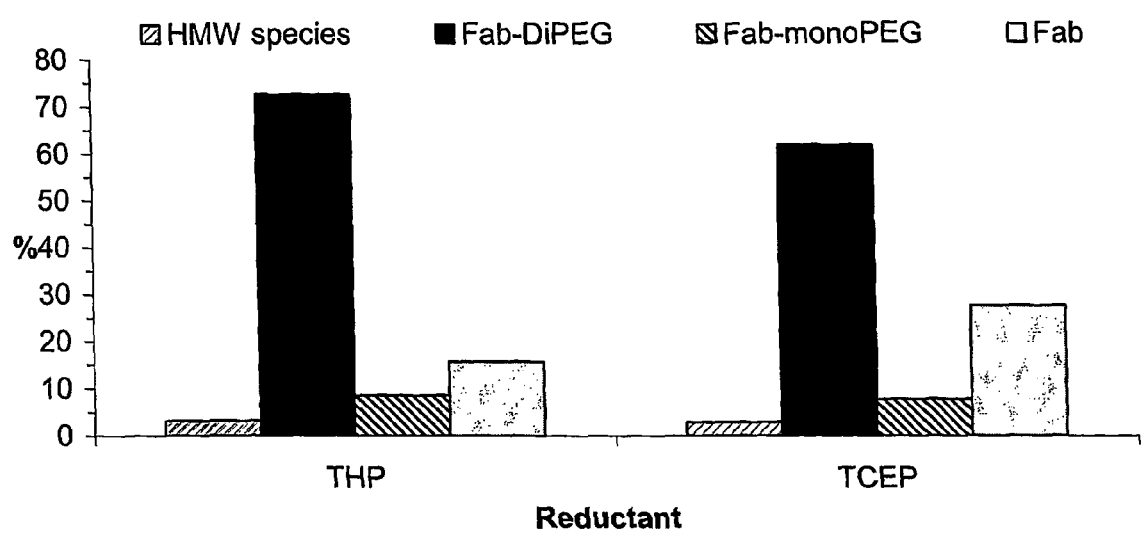

FIG. 2: Comparison of the reductants THP and TCEP on the PEGylation efficiency of Fab(B).

Figure 3:
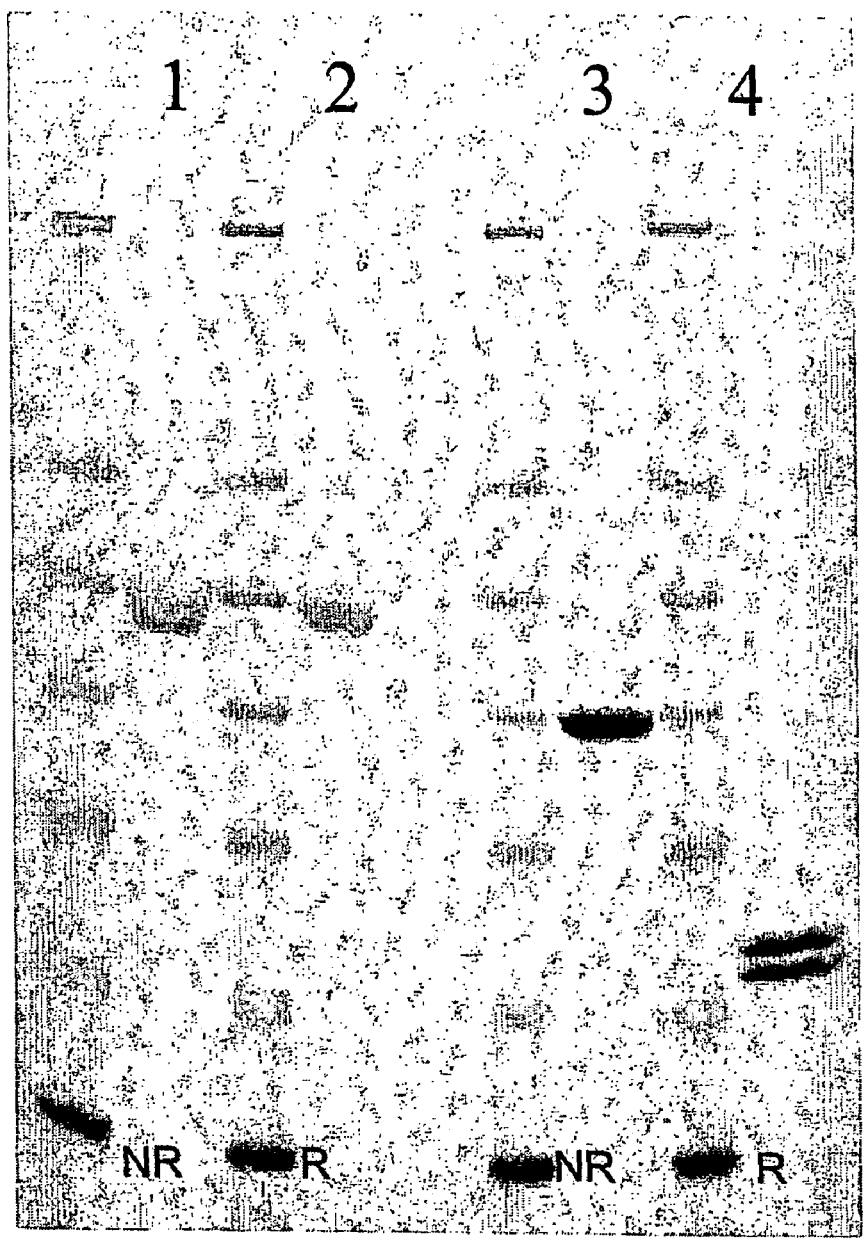

FIG. 3: SDS-PAGE of PEGylated murine Fab, m13.

Figure 4:
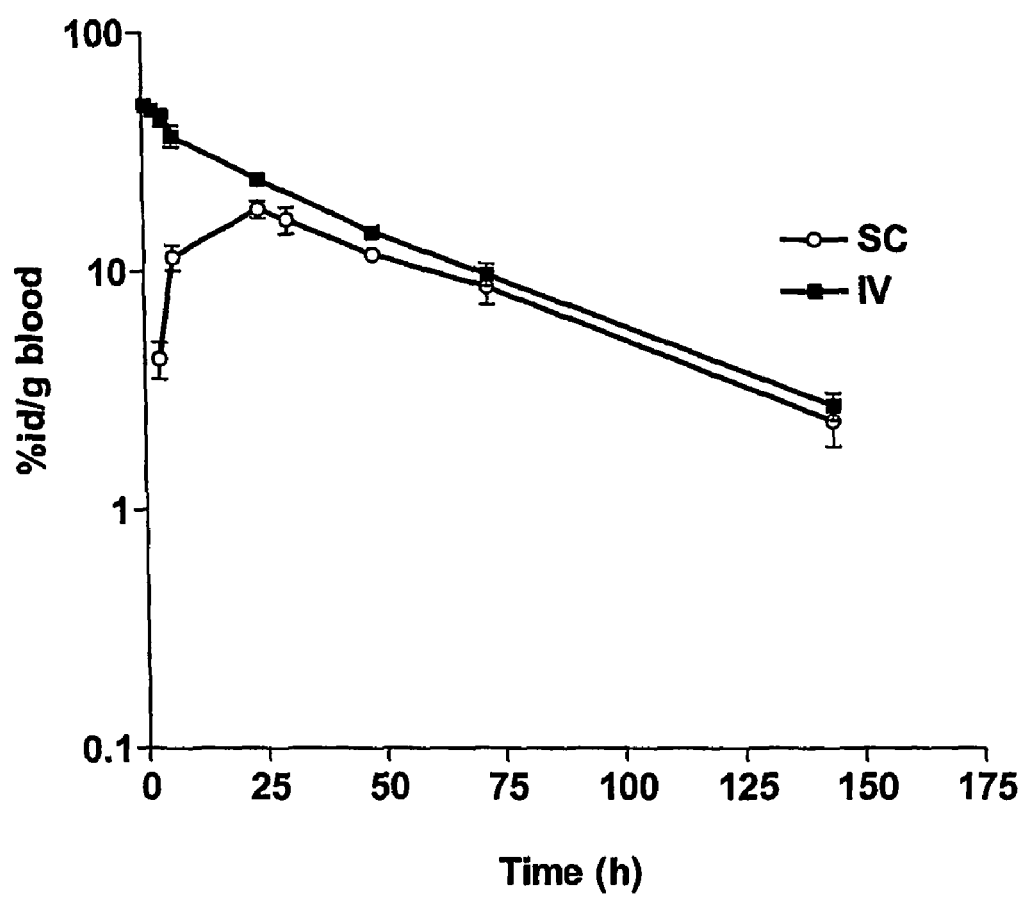

FIG. 4: Pharmacokinetics of $^{125}$I labelled m13 Fab-DiPEG (2×20 kDa) in mice.

FIG. 5 sets forth the sequence listings for SEQ ID NOS: 1-9 as described in the specification.

EXAMPLES

Example 1

Creation of a Novel 'Truncated' Fab Fragment

The antibody Fab molecule in Example 2 was g163 which binds to baboon platelet-derived growth factor receptor (PDGFr). The antibody Fab molecule in Examples 3-6 was a human Fab (herein after referred to as FAB(B)) which binds a soluble cytokine. The antibody Fab molecule in Examples 7-8 was a murine Fab, m13, which binds a soluble cytokine. To produce g163 and Fab(B) PCR primers were designed based on the human IgG1 $C_H1$ region and PCR mutagenesis used to insert a stop codon immediately following the interchain cysteine of $C_H1$. To produce m13 PCR primers were designed based on the murine IgG1 $C_H1$ region and PCR mutagenesis used to insert a stop codon immediately following the interchain cysteine of $C_H1$. The sequences of the heavy and light chain constant regions are shown below and in FIG. 5:

Wild Type Human γ1 Fab Constant Regions:

```
Kappa
KRTVAAPSVFIFPPSDEQLKSGTASVVCLLNNFYP    (Seq ID NO: 2)
REAKVQWKVDNALQSGNSQESVTEQDSKDSTYSLS
STLTLSKADYEKHKVYACEVTHQGLSSPVTKSFNR
GEC*

CH1
ASTKGPSVFPLAPSSKSTSGGTAALGCLVKDYFPE    (Seq ID NO: 9)
PVTVSWNSGALTSGVHTFPAVLQSSGLYSLSSVVT
VPSSSLGTQTYICNVNHKPSNTKVDKKVEPKSCDK
THTCAA*
```

Human 'Truncated' γ1 Fab Constant Regions Used in g163 and Fab(B):

```
Kappa
KRTVAAPSVFIFPPSDEQLKSGTASVVCLLNNFYP    (Seq ID NO: 2)
REAKVQWKVDNALQSGNSQESVTEQDSKDSTYSLS
STLTLSKADYEKHKVYACEVTHQGLSSPVTKSFNR
GEC*

CH1
ASTKGPSVFPLAPSSKSTSGGTAALGCLVKDYFPE    (SEQ ID NO: 1)
TPVVSWNSGALTSGVHTFPAVLQSSGLYSLSSVVT
VPSSSLGTQTYICNVNHKPSNTKVDKKVEPKSC*
```

Murine 'Truncated' γ1 Fab Constant Regions Used in m13:

```
Kappa
DAAPTVSIFPPSSEQLTSGGASVVCFLNNFYPKDI    (SEQ ID NO: 4)
NVKWKIDGSERQNGVLNSWTDQDSKDSTYSMSSTL
TLTKDEYERHNSYTCEATHKTSTSPIVKSFNRGE
C*

CH1
KTTPPSVYPLAPGSAAQTNSMVTLGCLVKGYFPEP    (SEQ ID NO: 3)
VTVTWNSGSLSSGVHTFPAVLQSDLYTLSSSVTVP
SSTWPSETVTCNVAHPASSTKVDKKIVPRDC*
```

The underlined cysteine residues indicate the interchain cysteines to which effector molecules may be attached.

The Fab fragments were produced in *E. coli* strain W3110 and purified using standard methods (Humphreys et al., 2002, Protein Expression and Purification, 26, 309-320).

Example 2

PEGylation of g163

All reductions and PEGylations were performed in 0.1 M Phosphate pH6.0; 2 mM EDTA. The concentration of Fab was 5 mg/ml and reductant was at 40 mM final concentration. In all cases reduction was performed at room temperature (~24° C.) for 30 minutes, the proteins desalted on a PD-10 column (Pharmacia) and then mixed with 5 fold molar excess of 20 kDa PEG-maleimide over Fab. The 20 kDa PEG was from Nippon Oils and Fats (NOF). PEGylated Fab was separated from unPEGylated Fab by size exclusion HPLC on analytical Zorbax GF-450 and GF-250 columns in series, These were developed with a 30 min isocratic gradient of 0.2 M phosphate pH 7.0+10% ethanol at 1 ml/min and Fab detected using absorbance at 214 nm and 280 nm.

The g163 Fab was reduced using two non thiol based reducing agents, tris(2-carboxyethyl)phosphine (TCEP), tris butyl phosphine (TBP) and two 20 kDa PEG molecules attached to the interchain cysteines. PEGylation was expected to occur on both cysteines if the inter-chain disulphide was reduced. The PEGylation of both sites was confirmed by non-reducing SDS-PAGE (FIG. 1). Lane B corresponds to g163 truncated Fab with two PEG molecules attached following reduction with TCEP. The two high molecular weight bands very close together around 100 kDa are composed of heavy and light chain with one PEG molecule attached. The lower band at around 45 kDa is a small amount of unmodified Fab with no PEG attached. The lower band at around 25 kDa is free heavy and light chains. Lane D is the same fragment reduced using TBP that is less compatible with aqueous buffers and proteins. The percentage of the g163 truncated Fab to be diPEGylated using TCEP and TBP as reductants was 76% and 21% respectively, as determined by HPLC. TCEP is therefore a useful reducing agent for producing the modified antibody fragments of the present invention.

Example 3

Comparison of Efficiency of PEGylation of Fab(p) using the Reducing Agents TCEP and THP In this example reductions and PEGylations were conducted in 50 mM MOPS, 2 mM EDTA pH6.8. Reduction of Fab(B) (20 mg/ml) was performed using reducing agents TCEP or ThP at 10 mM, for 1 hr at ambient temperature. Reductant was removed on PD10 desalting columns (Pharmacia) with a stringent cut to prevent carry over of the reductant. PEGylation was conducted using 3 fold molar excess of 20 kDa PEG-maleimide over Fab, over night at ambient temperature. FIG. 2 shows that THP is also a useful reducing agent for attaching PEG to the antibody fragments of the present invention.

Example 4

Di-Pegylation of a Murine Fab, m13

The interchain cysteines of a murine truncated Fab, m13 were PEGylated using 20 kDa linear PEG. Reductions and PEGylations were performed in 50 mM Tris.HCl 5 mM EDTA pH 7.14 with Fab at 20.06 mg/ml, 10 mM TCEP (final) and 4 molar excess of 20 kDa linear PEG, room temperature. The PEGylation of both sites was confirmed by SDS-PAGE (FIG. 3). Lane 1 m13 diPegylated (non-reduced); Lane 2 m13 dipegylated reduced; Lane 3 m13 non-reduced (no PEG); Lane 4 m13 reduced (no PEG).

Example 5

Pharmacokinetics of m13 Fab-PEG (2×20 kDa) in Mice

The circulating half life of m13Fab PEGylated on both polypeptides (as in Example 4) in animals was determined. $^{125}$I labelled PEGylated Fab molecules were injected subcutaneously or intravenously into mice and the serum permanence determined.

Mice were injected subcutaneously on the back of the neck or intravenously in the tail vein under light anaesthesia. The injection volume was 100 µl per mouse which was equivalent to 13 µg protein and 1.2 µCi isotope dose (specific activity 0.1 µCi/µg). 4 mice were bled by cardiac puncture at each time point. Heparanised blood was collected in preweighed tubes. The weight of the blood was determined before counting for radioactivity in the gamma counter.

Time points studied:

iv; 0.5, 2, 4, 6, 24, 48, 72 and 144 h post injection.

sc; 3, 6, 24, 30, 48, 72 and 144 h post injection.

TABLE 1

|  | IV | SC |
| --- | --- | --- |
| AUC (0-∞) (% dose * h) | 3147 | 2072 |
| T½ β (h) | 37 | 41 |
| Cmax(% dose) |  | 26 |

The results in Table 1 and FIG. 4 show that although the heavy and light chains in the PEGylated Fab are non-covalently associated the circulating half life is higher than a non-PEGylated Fab (t½β≈30 minutes) and that of free LC or HC which is likely to be shorter still.

The invention claimed is:

1. An antibody Fab fragment comprising a heavy chain constant region that terminates at the interchain cysteine of $C_H1$.

2. The antibody Fab fragment of claim 1 wherein the interchain cysteine of $C_H1$ is covalently linked to the interchain cysteine of $C_L$.

3. The antibody Fab fragment of claim 1 wherein the interchain cysteine of $C_H1$ is at position 233 of the heavy chain of human IgG1, according to the Kabat numbering system.

4. The antibody Fab fragment of claim 1 wherein the interchain cysteine of $C_H1$ is at position 127 of the heavy chain of human IgM, IgE, IgG2, IgG3, or IgG4, according to the Kabat numbering system.

5. The antibody Fab fragment of claim 1 wherein the interchain cysteine of $C_H1$ is at position 128 of the heavy chain of human IgD or IgA2B, according to the Kabat numbering system.

6. The antibody Fab fragment of claim 1 wherein the interchain cysteine of $C_H1$ is at position 235 of the heavy chain of murine IgG, according to the Kabat numbering system.

7. The antibody Fab fragment of claim 1 wherein the interchain cysteine of the light chain constant region is at position 214 of the light chain of human IgG1 or murine IgG, according to the Kabat numbering system.

8. The antibody Fab fragment of claim 1 that has been modified by attachment of one or more effector molecules.

9. The antibody Fab fragment of claim 8 that has been modified by attachment of two or more effector molecules.

10. The antibody fragment of claim 9 wherein an effector molecule is attached to a cysteine in the light chain constant region and to a cysteine in the heavy chain constant region.

11. The antibody fragment of claim 10 wherein the cysteine residues in the heavy and light chain constant regions that are attached to effector molecules would otherwise be linked to each other via a disulphide bond if the effector molecules were not attached.

12. The antibody fragment of claim 11 wherein the light chain cysteine to which an effector molecule is attached is the interchain cysteine of $C_L$ and the heavy chain cysteine to which an effector molecule is attached is the interchain cysteine of $C_H1$.

13. The antibody Fab fragment of claim 8 wherein the effector molecule is PEG.

14. A composition comprising a mixture of two or more antibody Fab fragments wherein the mixture is enriched for the Fab fragments comprising a heavy chain constant region that terminates at the interchain cysteine of $C_H1$, and in which the heavy chains in the fragments are not covalently bonded to the light chains and the fragments have an effector molecule attached to a cysteine in the light chain constant region and the heavy chain constant region of the fragments.

15. The composition of claim 14 wherein greater than 50% of the mixture comprises the Fab fragments comprising a heavy chain constant region that terminates at the interchain cysteine of $C_H1$, and in which the heavy chains in the fragments are not covalently bonded to the light chains and the fragments have an effector molecule attached to a cysteine in the light chain constant region and the heavy chain constant region of the fragments.

16. A composition comprising an antibody Fab fragment of claim 1, together with one or more pharmaceutically acceptable excipients, diluents or carriers.

* * * * *

UNITED STATES PATENT AND TRADEMARK OFFICE
CERTIFICATE OF CORRECTION

PATENT NO.         : 7,989,594 B2
APPLICATION NO.    : 10/562746
DATED              : August 2, 2011
INVENTOR(S)        : Humphreys et al.

It is certified that error appears in the above-identified patent and that said Letters Patent is hereby corrected as shown below:

On the Title Page, Item (73) Assignee should read --

(73) Assignee:   UCB Pharma S. A., Brussels, Belgium

Signed and Sealed this
Twenty-third Day of July, 2013

Teresa Stanek Rea
*Acting Director of the United States Patent and Trademark Office*

SEQUENCE LISTING

```
<160> NUMBER OF SEQ ID NOS: 9

<210> SEQ ID NO 1
<211> LENGTH: 103
<212> TYPE: PRT
<213> ORGANISM: Artificial Sequence
<220> FEATURE:
<223> OTHER INFORMATION: Synthetic

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

<210> SEQ ID NO 2
<211> LENGTH: 108
<212> TYPE: PRT
<213> ORGANISM: Artificial Sequence
<220> FEATURE:
<223> OTHER INFORMATION: Synthetic

<400> SEQUENCE: 2

```
Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105
```

<210> SEQ ID NO 3
<211> LENGTH: 101
<212> TYPE: PRT
<213> ORGANISM: Artificial Sequence
<220> FEATURE:
<223> OTHER INFORMATION: Synthetic

<400> SEQUENCE: 3

```
Lys Thr Thr Pro Pro Ser Val Tyr Pro Leu Ala Pro Gly Ser Ala Ala
1               5                   10                  15

Gln Thr Asn Ser Met Val Thr Leu Gly Cys Leu Val Lys Gly Tyr Phe
            20                  25                  30

Pro Glu Pro Val Thr Val Thr Trp Asn Ser Gly Ser Leu Ser Ser Gly
        35                  40                  45

Val His Thr Phe Pro Ala Val Leu Gln Ser Asp Leu Tyr Thr Leu Ser
    50                  55                  60

Ser Ser Val Thr Val Pro Ser Ser Thr Trp Pro Ser Glu Thr Val Thr
65                  70                  75                  80

Cys Asn Val Ala His Pro Ala Ser Ser Thr Lys Val Asp Lys Lys Ile
                85                  90                  95

Val Pro Arg Asp Cys
            100
```

<210> SEQ ID NO 4
<211> LENGTH: 105
<212> TYPE: PRT
<213> ORGANISM: Artificial Sequence
<220> FEATURE:
<223> OTHER INFORMATION: Synthetic

<400> SEQUENCE: 4

```
Asp Ala Ala Pro Thr Val Ser Ile Phe Pro Pro Ser Ser Glu Gln Leu
1               5                   10                  15

Thr Ser Gly Gly Ala Ser Val Val Cys Phe Leu Asn Asn Phe Tyr Pro
            20                  25                  30

Lys Asp Ile Asn Val Lys Trp Lys Ile Asp Gly Ser Glu Arg Gln Asn
```

```
                35                  40                  45
Gly Val Leu Asn Ser Trp Thr Asp Gln Asp Ser Lys Asp Ser Thr Tyr
 50                  55                  60
Ser Met Ser Ser Thr Leu Thr Leu Thr Lys Asp Glu Tyr Glu Arg His
 65                  70                  75                  80
Asn Ser Tyr Thr Cys Glu Ala Thr His Lys Thr Ser Thr Ser Pro Ile
                 85                  90                  95
Val Lys Ser Phe Asn Arg Gly Glu Cys
            100                 105
```

<210> SEQ ID NO 5
<211> LENGTH: 312
<212> TYPE: DNA
<213> ORGANISM: Artificial Sequence
<220> FEATURE:
<223> OTHER INFORMATION: Synthetic

<400> SEQUENCE: 5

```
gcttctacaa agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tcgacaagaa agttgagccc   300
aaatcttgtt aa                                                       312
```

<210> SEQ ID NO 6
<211> LENGTH: 327
<212> TYPE: DNA
<213> ORGANISM: Artificial Sequence
<220> FEATURE:
<223> OTHER INFORMATION: Synthetic

<400> SEQUENCE: 6

```
aaacgtacgg tagcggcccc atctgtcttc atcttcccgc catctgatga gcagttgaaa    60
tctggaactg cctctgttgt gtgcctgctg aataacttct atcccagaga ggccaaagta   120
cagtggaagg tggataacgc cctccaatcg gtaactccc aggagagtgt cacagagcag   180
gacagcaagg acagcaccta cagcctcagc agcaccctga cgctgagcaa agcagactac   240
gagaaacaca aagtctacgc ctgcgaagtc acccatcagg gcctgagctc accagtaaca   300
aaaagttta tagagggga gtgttaa                                          327
```

<210> SEQ ID NO 7
<211> LENGTH: 306
<212> TYPE: DNA
<213> ORGANISM: Artificial Sequence
<220> FEATURE:
<223> OTHER INFORMATION: Synthetic

<400> SEQUENCE: 7

```
aaaacgacac ccccatctgt ctatccactg gcccctggat ctgctgccca aactaactcc    60
atggtgaccc tgggatgcct ggtcaagggc tatttccctg agccagtgac agtgacctgg   120
aactctggat ccctgtccag cggtgtgcac accttcccgg ctgtcctgca atctgacctc   180
tacactctga gcagctcagt gactgtcccc tccagcacct ggcccagcga gaccgtcacc   240
tgcaacgttg cccacccggc cagcagcacc aaggtggaca gaaaaattgt gcccagggat   300
tgttaa                                                              306
```

<210> SEQ ID NO 8
<211> LENGTH: 318
<212> TYPE: DNA
<213> ORGANISM: Artificial Sequence
<220> FEATURE:
<223> OTHER INFORMATION: Synthetic

<400> SEQUENCE: 8

```
gatgctgcac caactgtatc catcttccca ccatccagtg agcagttaac atctggaggt      60
gcctcagtcg tgtgcttctt gaacaacttc tacccaaag acatcaatgt caagtggaag     120
attgatggca gtgaacgaca aaatggcgtc ctgaacagtt ggactgatca ggacagcaaa    180
gacagcacct acagcatgag cagcaccctc acgttgacca aggacgagta tgaacgacat    240
aacagctata cctgtgaggc cactcacaag acatcaactt cacccattgt caaaagcttt    300
aatagagggg agtgttaa                                                   318
```

<210> SEQ ID NO 9
<211> LENGTH: 111
<212> TYPE: PRT
<213> ORGANISM: Artificial Sequence
<220> FEATURE:
<223> OTHER INFORMATION: Synthetic

<400> SEQUENCE: 9

```
Ala Ser Thr Lys Gly Pro Ser Val Phe Pro Leu Ala Pro Ser Ser Lys
1               5                  10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Ala Ala
            100                 105                 110
```